US009688433B2

(12) United States Patent
Camedda et al.

(10) Patent No.: US 9,688,433 B2
(45) Date of Patent: Jun. 27, 2017

(54) PRIMARY PACKAGING FOR A STERILE MEDICAL DEVICE

(71) Applicant: Peters Surgical, Bobigny (FR)

(72) Inventors: Caroline Camedda, Groslay (FR); Nathalie Van Landeghem, Paris (FR)

(73) Assignee: Peters Surgical (FR)

( * ) Notice: Subject to any disclaimer, the term of this patent is extended or adjusted under 35 U.S.C. 154(b) by 0 days.

(21) Appl. No.: 14/653,647

(22) PCT Filed: Dec. 20, 2013

(86) PCT No.: PCT/EP2013/077862
§ 371 (c)(1),
(2) Date: Jun. 18, 2015

(87) PCT Pub. No.: WO2014/096434
PCT Pub. Date: Jun. 26, 2014

(65) Prior Publication Data
US 2015/0307223 A1 Oct. 29, 2015

(30) Foreign Application Priority Data
Dec. 20, 2012 (FR) .................................... 12 62468

(51) Int. Cl.
*B65D 5/10* (2006.01)
*A61F 15/00* (2006.01)
*A61B 17/06* (2006.01)
*A61F 13/00* (2006.01)
*B65D 65/10* (2006.01)
(Continued)

(52) U.S. Cl.
CPC .......... *B65D 5/10* (2013.01); *A61B 17/06138* (2013.01); *A61B 46/00* (2016.02);
(Continued)

(58) Field of Classification Search
CPC ... A61B 17/06; A61B 17/06138; A61B 19/02; A61B 19/26; A61B 46/00; A61B 50/30; A61B 2019/024; A61B 2019/0267; A61B 2050/0084; A61B 2050/314; A61F 13/00; A61F 13/00085; A61F 15/00; A61F 15/001; B65D 5/10; B65D 27/22; B65D 27/36; B65D 65/10; B65D 65/22; B65D 75/14
(Continued)

(56) References Cited

U.S. PATENT DOCUMENTS 2,985,288 A * 5/1961 Reich ................. A61B 10/0096
206/363
4,019,633 A * 4/1977 Roth ..................... B65D 5/503
206/364
(Continued)

OTHER PUBLICATIONS

International Search Report and Written Opinion for Application No. PCT/EP2013/077862 dated Feb. 3, 2014.
(Continued)

*Primary Examiner* — Bryon Gehman
(74) *Attorney, Agent, or Firm* — Lerner, David, Littenberg, Krumholz & Mentlik, LLP

(57) ABSTRACT

The present invention is directed to packaging for an item of medical equipment. The packaging includes a sheet for receiving the contents, a cover element and closing mechanism. The packaging is simple to manufacture, reliable, allows easy and safe access to the medical equipment, and without any particular excess cost.

14 Claims, 10 Drawing Sheets

(51) Int. Cl.
    *B65D 75/14* (2006.01)
    *B65D 27/22* (2006.01)
    *B65D 27/36* (2006.01)
    *A61B 46/00* (2016.01)
    *A61B 50/00* (2016.01)
    *A61B 50/30* (2016.01)

(52) U.S. Cl.
    CPC ........ *A61B 50/30* (2016.02); *A61F 13/00085* (2013.01); *A61F 15/001* (2013.01); *B65D 27/22* (2013.01); *B65D 27/36* (2013.01); *B65D 65/10* (2013.01); *B65D 75/14* (2013.01); *A61B 2050/0084* (2016.02); *A61B 2050/314* (2016.02)

(58) Field of Classification Search
    USPC ................. 206/363, 364, 438, 439; 229/87.01–87.06
    See application file for complete search history.

(56) References Cited

U.S. PATENT DOCUMENTS

| | | | | |
|---|---|---|---|---|
| 4,332,322 A | * | 6/1982 | Jaeschke | ............... B65D 75/20 206/363 |
| 4,342,392 A | | 8/1982 | Cox | |
| 4,615,435 A | | 10/1986 | Alpern et al. | |
| 5,050,735 A | * | 9/1991 | Levy | ..................... B65D 75/14 206/363 |
| 7,694,813 B2 | * | 4/2010 | Shalaby | ............... B65D 75/14 206/438 |

OTHER PUBLICATIONS

French Preliminary Search Report and Written Opinion for Application No. FR1262468 dated Jul. 9, 2013.

* cited by examiner

PRIMARY PACKAGING FOR A STERILE MEDICAL DEVICE

CROSS REFERENCE TO RELATED APPLICATIONS

The present application is a national phase entry under 35 U.S.C. §371 of International Application No. PCT/EP2013/077862, filed Dec. 20, 2013, published in French, which claims priority from French Patent Application No. 1262468, filed Dec. 20, 2012, the disclosures of which are incorporated by reference herein.

FIELD OF THE INVENTION

The invention relates to the field of packaging for items of medical equipment.

It relates to many applications for medical purposes. However, it is particularly applicable to gauze tents or knits used in surgery, without being limited thereto.

PRIOR ART

Many types of packaging designed to contain items of medical equipment have already been proposed.

To reduce contamination risks, surgical equipment is generally preserved in aseptic packaging. However, once such a packaging is open, the item of equipment contained inside is no longer in an aseptic environment.

In some cases, the practitioner opens the packaging themselves before taking hold of and using the medical equipment it contains.

In other cases, during a surgical operation for example, the packages are first opened by medical staff, and their contents are then handed to the practitioner who can take hold of the contents.

In all cases, the opening of the package and then the extraction of its contents must require a minimum amount of handling of the packaging itself, it being necessary to perform this handling in such a way that the sterile nature of the contents is guaranteed.

A known example of packaging is described in the document U.S. Pat. No. 4,342,392. This document describes a packaging made by folding a sheet so as to form a cradle for receiving the contents, made of two flaps hinged together in the shape of a clamp, a cover element hinged on one of the flaps of the cradle and closing means, themselves hinged transversely on the flaps of the cradle and/or the cover element. The closing means are fastened by sealing. The appended FIG. 1 schematically illustrates a step in the opening of such a packaging after separating and deploying the side closing means.

An examination of the FIG. 1 will show that the use of such a packaging does not give full satisfaction insofar as it is difficult to open because part of it must be carried out blind, one of the hands of the operator holding the clamp-shaped cradle which encases the contents to be picked up, while the other hand must be positioned under the packaging in order to take hold of the cover element to deploy it.

Overview of the Invention

The aim of the invention is to improve on the known techniques of the prior art.

In particular, the aim of the invention is to propose a new packaging which, while being simple to manufacture and reliable, allows easy and safe access to the contents, without any particular excess cost.

This aim is achieved according to the present invention with a packaging for an item of medical equipment produced by folding a sheet so as to form a cradle for receiving the content, made of two flaps hinged together in the shape of a clamp, a cover element hinged on one of the flaps of the cradle and closing means, themselves hinged transversely on at least one of the flaps of the cradle and/or the cover element, characterized by the fact that the closing means are designed to be fixed together by simple mechanical engagement between them and that, when urged to open, the cover element exerts a force on said closing means mechanically engaged with each other, making them automatically separate and thus opening the packaging.

One advantage of the present invention is that the opening of the packaging is carried out in a single, instinctive, and fast hand gesture, without any risk of the handler directly touching the contents of the packaging.

Another advantage lies in the fact that no additional fastening means such as glue, adhesive or any other kind are required to close the packaging.

The invention is advantageously completed by the following features, taken alone or in any technical possible combination:

- at least one of the closing means is hinged transversely on the cover element by a transverse fold line,
- at least one of the closing means is a driving closing means hinged transversely on one of the flaps of the cradle and on the cover element by a driving transverse fold line,
- the cover element is hinged to a base flap of the cradle by a longitudinal fold line secant with each transverse fold line,
- each driving closing means is traversed by an extension of the longitudinal fold line of the closing element on the base flap, allowing it to form a dihedron when the cover element is in the folded position,
- the packaging includes two closing means, at least the first of which is a driving closing means in the shape of a dihedron, the mechanical engagement between them in their folded position being effected by encasing a section of the second closing means within the dihedron formed by the first driving closing means,
- both closing means are driving and in the shape of a dihedron, both driving transverse fold lines are perpendicular to the longitudinal fold line of the cover element on the base flap, and the edges of the dihedrons touch each other in at least one segment when the closing means are engaged inside each other in their folded position,
- the cover element includes a covering flap comprising a free edge opposite a longitudinal fold line, wherein is formed at least one notch leaving a section of the surface of the cradle uncovered when the cover element is in the folded position,
- the cover element includes a covering flap comprising at least one transverse edge including a transverse section connected to a closing means and a free transverse section adjacent to a free edge,
- the closing means are folded down against the cradle and partly cover it in such a way as to leave a section of the surface on the cradle uncovered,
- the cradle includes a protective flap folded down on a base flap by a protective fold line, the two surface sections left uncovered on the cradle extending on either side of this protective fold line so as to be simultaneously taken hold of in a clamping movement, at least one driving closing means is symmetrical with respect to the extension of a longitudinal fold line that traverses it, in such a way that the two faces of the dihedron that it forms when the cover element is in the folded position coincide, the packaging is made of a non-woven textile material, preferably polyethylene fiber.

DESCRIPTION OF THE FIGURES

FIGS. 4 to 7 represent various steps of preparation of a packaging according to the embodiment illustrated in FIG. 3:

FIG. 4 is a front perspective view of the aforementioned packaging, whose receiving cradle is in the process of being shaped;

FIG. 5 is a front perspective view of the aforementioned packaging, with the shaping of its holding cradle finished, before the folding of the cover element;

FIG. 6 represents a front perspective view of the aforementioned packaging, with the cover element in folded position;

FIG. 9a represents a front view of the aforementioned packaging, wherein the cover element is stressed;

FIG. 9b represents a front view of the aforementioned packaging, with the closing means in the process of unfolding;

FIG. 9c represents a front perspective view of the aforementioned packaging, in the open position, permitting access to its contents.

Figure 14A:
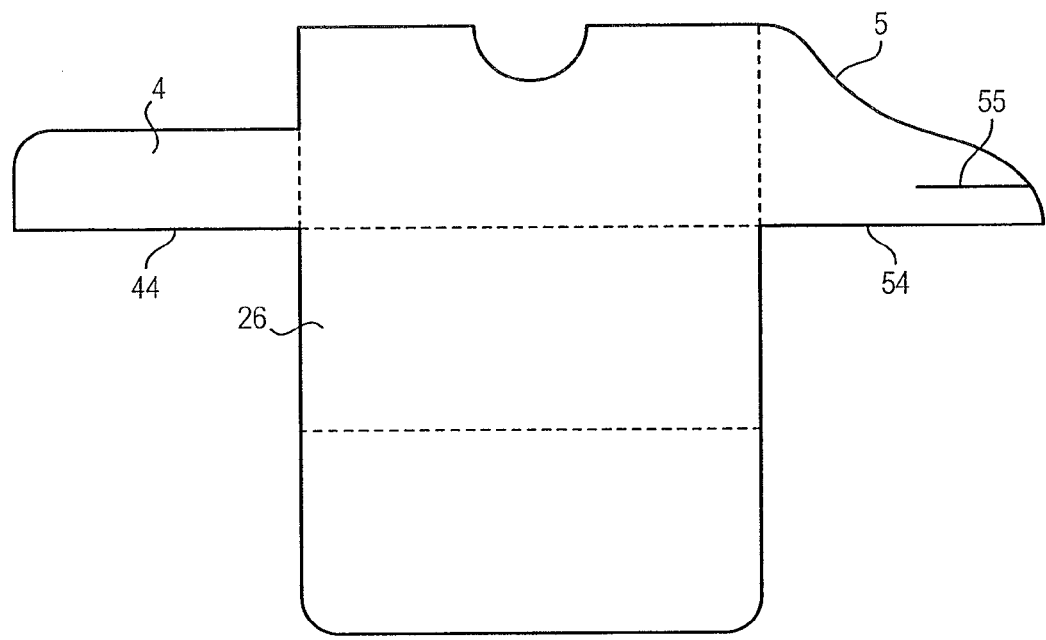
Figure 14B:
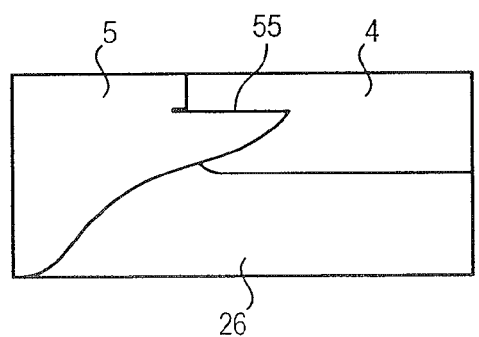
Figure 15:
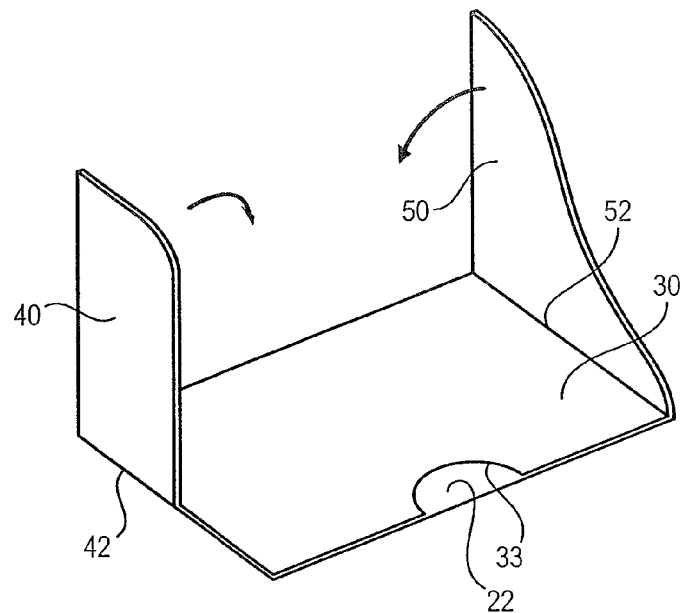
Figure 16:
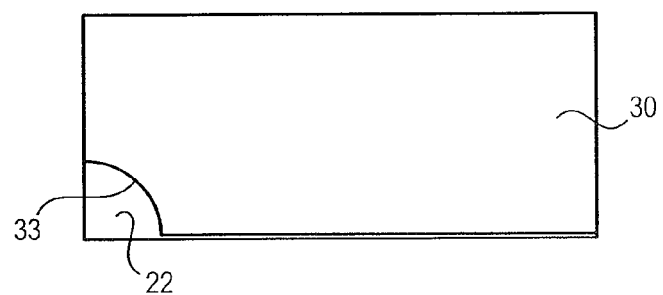
Figure 17:
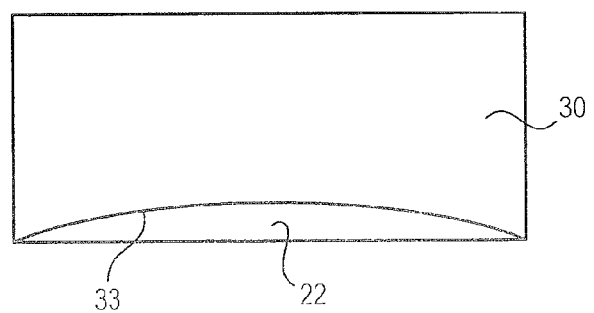

the variants illustrated in FIGS. 10 to 13 are outlines in top view, before they are shaped;

FIGS. 14a and 14b represent a same variant embodiment, in top view before shaping, and in back view after shaping, respectively;

FIG. 15 illustrates a variant embodiment during folding from a top perspective view;

FIGS. 16 and 17 represent variants in top view.

DETAILED DESCRIPTION OF THE INVENTION

A preferred embodiment will first be detailed, illustrated in FIGS. 2 to 9c.

Figure 3:
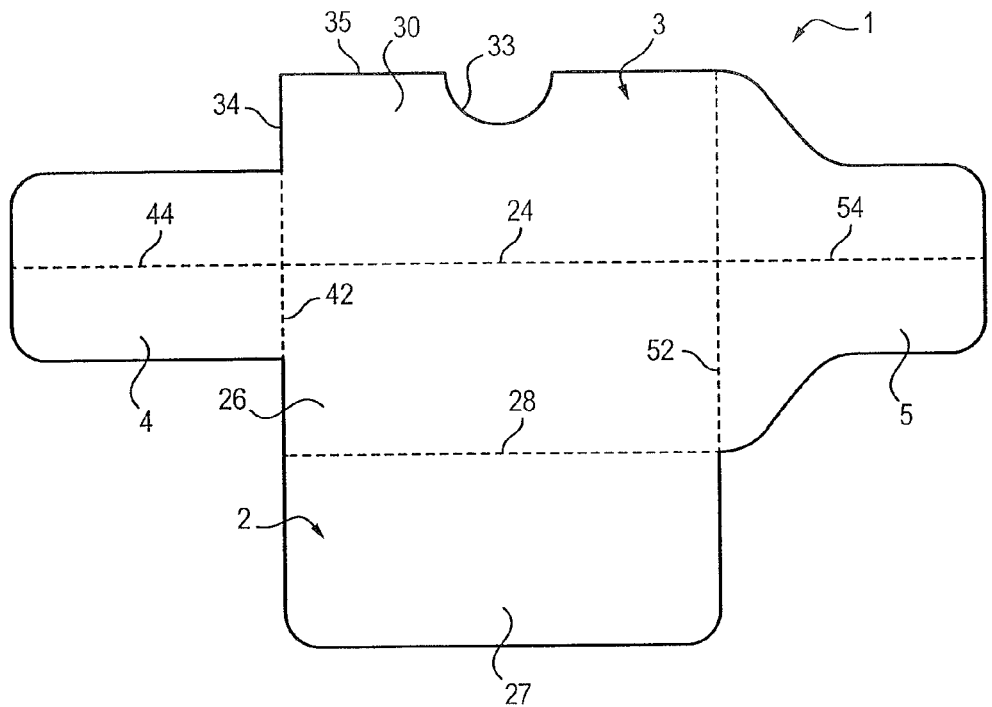
FIG. 3 represents an outline of the same embodiment in top view before shaping by folding.

The packaging 1 is made from a sheet, cut and folded to form several parts providing different functions illustrated in FIG. 3: a receiving cradle 2 intended to house and isolate M from any outside contact, a cover element 3 movable in relation to the housing cradle, and making it possible to shut the housing cradle, and closing means 4, 5 capable of holding the packaging closed.

The housing cradle 2 can consist of two flaps: a base flap 26 and a protective flap 27 hinged with the base flap 26 by a protective fold line 28 allowing the receiving cradle to form a clamp. The base 26 and protective 27 flaps have substantially rectangular outlines, the protective fold line 28 being placed on one of their long sides. Where applicable the protective flap 27 has both angles opposite the fold line of the protective fold line 28 rounded. Moreover, the protective flap 27 can have a width, taken perpendicular to the fold line 28, less than that of the base flap 26. Once folded about the fold line 28, the protective flap 27 covers the base flap 26, the contents M to be protected being placed in a casing 20 formed between the base flap 26 and the protective flap 27.

The cover element 3 is hinged with the base flap 26 of the receiving cradle 2 along a longitudinal folding line 24 located on an opposite edge to that of the protective fold line 28, and preferably parallel to it.

The cover element 3 comprises a covering flap 30, which itself includes a free edge 35 opposite the edge where the longitudinal fold line 24 is found.

The covering flap 30 preferably has an outline substantially identical to that of the base flap 26, advantageously rectangular, such as for example in the embodiment illustrated in FIG. 3. Once folded about the fold line 24, the covering flap 30 covers the protective flap 27 and consequently the receiving cradle 2 housing the contents M.

Figure 1:
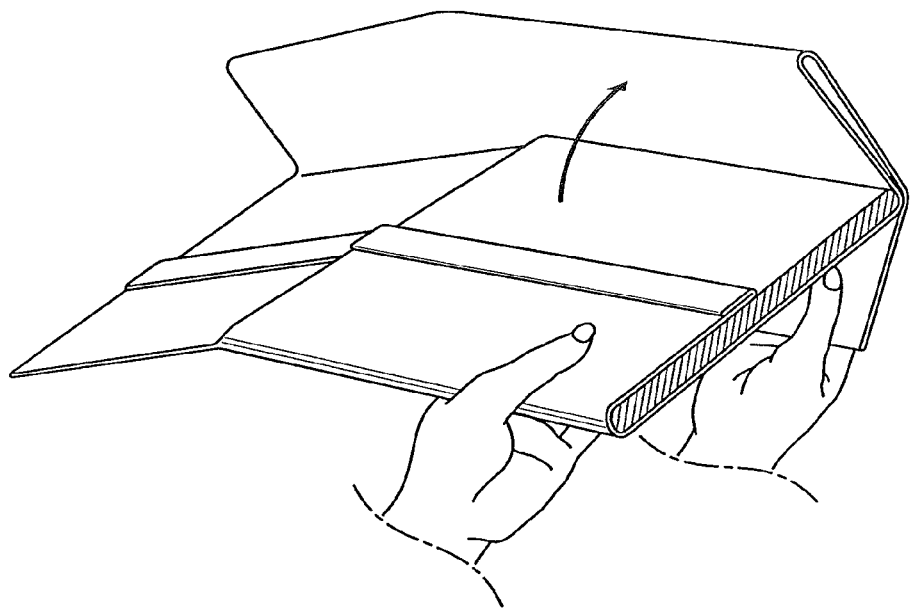
FIG. 1 shows the known packaging described above.
Figure 2:
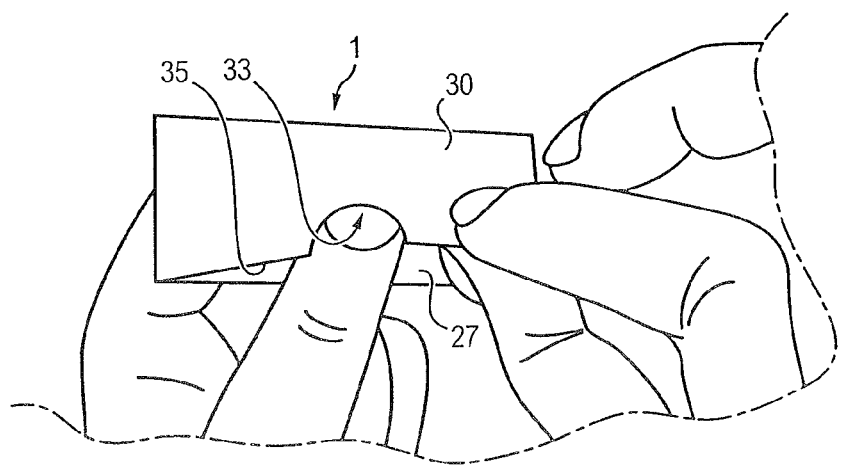
FIG. 2 represents a preferred embodiment of the invention seen in top view and handled manually.

However, the free edge 35 of the covering flap 30 is preferably not rectilinear but has a recess 33 allowing access to the underlying cradle 2. For example, the covering flap 30 is recessed on its free edge 35 by at least one notch 33 of any shape but of a suitable size to let through the end of a gripping tool, or the finger of a handler as seen in FIG. 2, to take hold of the underlying cradle 2.

Each closing means 4, 5 is connected to at least one of the flaps of the receiving cradle 2 (preferably the base flap 26), and/or to the cover element 3.

In particular, the term "driving" closing means refers to a closing means which is connected to at least one covering flap 30 of the cover element 3. Below it will be seen that such a closing means provides a function of transmission of mechanical force during the opening of the packaging.

Preferably, the packaging includes at least one driving closing means; the embodiment illustrated in FIGS. 2 to 9c contains two thereof.

More precisely, the closing means 4, 5 are preferably each formed of tabs hinged with the base flap 26 and the covering flap 30, around respective fold lines 42, 52, advantageously mutually parallel and orthogonal to the aforementioned fold lines 24 and 28.

Extensions 44, 54 of the longitudinal fold line 24 traverse the driving closing means 4, 5 thus dividing each of them into two sections, one connected to the covering flap 30 and the other to the base flap 26. In a preferred but non-limiting way, each driving closing means 4, 5 is symmetrical with respect to the extension 44, 54 of the longitudinal fold line 24 that traverses it. Moreover, these closing means 4, 5 can have identical or different shapes.

The driving closing means 5 represented on the right in FIG. 3 extends along a whole transverse edge of the covering flap 30 and a whole transverse edge of the base flap 26 and gradually tapers into a point shape at a distance from the fold line 52.

The driving closing means 4 represented on the left in FIG. 3 is in the shape of a rectangular tab. Unlike the closing means 5, it covers only part of the transverse edge of the covering flap 30 and only part of the transverse edge of the base flap 26, leaving only a section of free transverse edge on the base flap 26 and a section of free transverse edge of the same length on the covering flap 30, both sections of free transverse edge being opposite in relation to the extension 44 of the longitudinal fold line 24.

In summary, the outline represented in FIG. 3 comprises a base flap 26 on either side of which the protective flap 27 to form the receiving cradle 2 and the covering flap 30, and two tabs 4, 5 hinged with the transverse edges of the base flaps 26 and covering flaps 30 about the respective fold lines 42, 52 orthogonal to the fold line 24 are respectively hinged about folding lines 28 and 24.

There now follows a description of the steps of folding of the packaging 1 according to the invention, once the planar outline represented in FIG. 3 has been cut out around the described perimeter.

Figure 4:
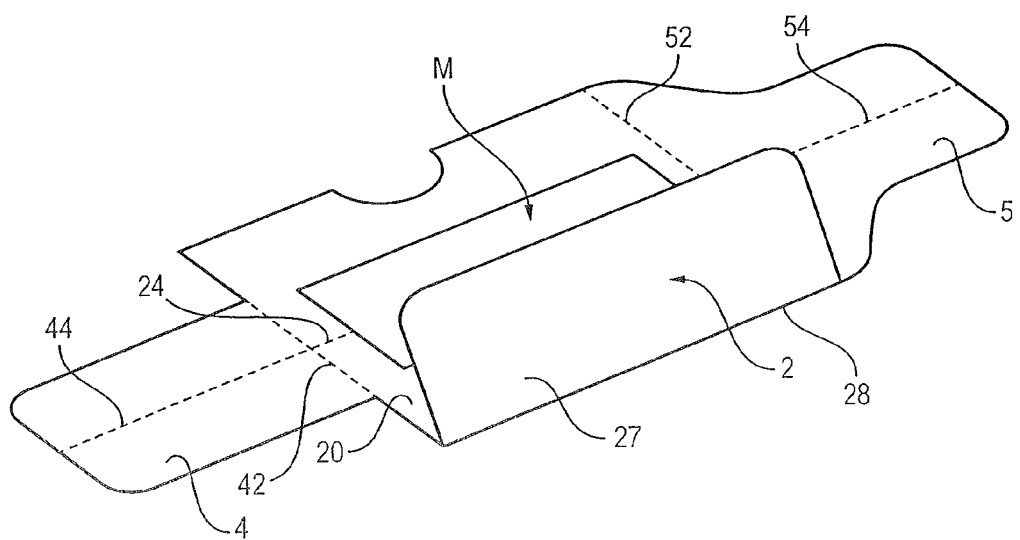
Figure 5:
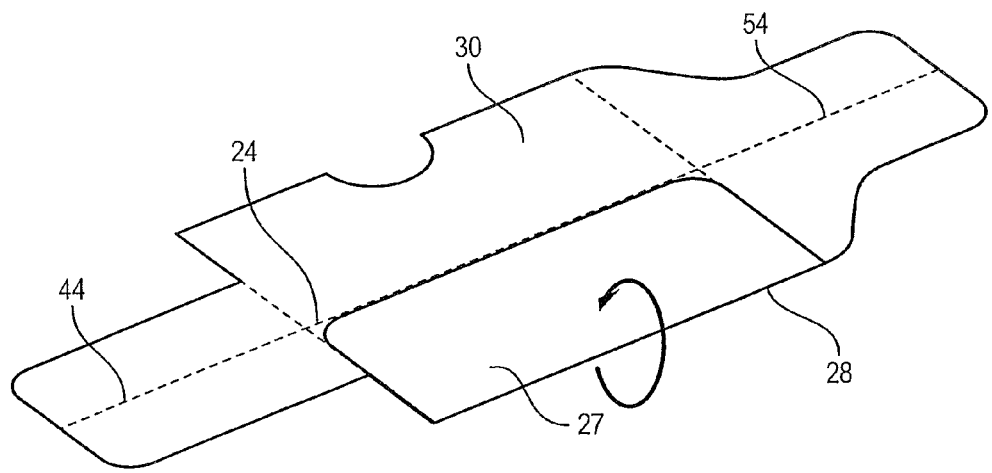

The covering flap 27 is first folded along the protective fold line 28 as illustrated in FIG. 4. The space between the base flap 26 and the protective flap 27 then forms a casing 20 designed to house the contents M and isolate it from the outside.

The covering flap 30 is then folded with respect to the longitudinal fold line 24 on the protective flap 27. In the same movement, the driving closing means are folded back on themselves about the extensions 44, 54 of the longitudinal fold line 24, which gives them the shape of a dihedron 40, 50.

Figure 6:
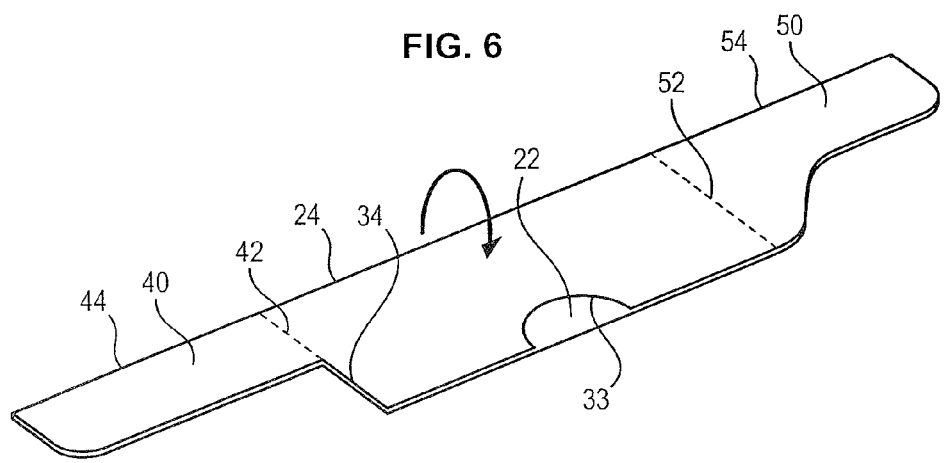

Once the covering flap 30 is resting against the protective flap 27, the cover element 3 is in a folded position wherein the dihedrons 40, 50 are substantially flat and the notch 33 on the covering flap 30 leaves uncovered a first section of the surface 22 of the protective flap 27, as illustrated in FIG. 6. Note that the protective flap 27 is adapted to cover a surface comprising at least this first surface section 22 left uncovered, in such a way as to prevent direct access to the casing 20 from the notch 33.

Figure 7A:
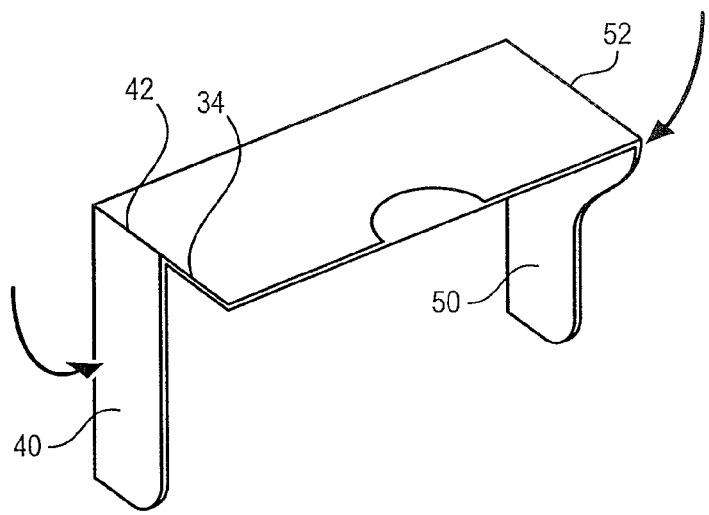
FIGS. 7a and 7b respectively represent a front perspective view and a back view of the aforementioned packaging, with its closing means in the process of being closed.

With reference to FIG. 7a, the closing means 4, 5 are then folded along the respective longitudinal fold lines 42, 52 secant with the longitudinal fold line 24 or even perpendicular to it in the illustrated embodiment as stated previously.

Hereinafter, the term "driving longitudinal fold line" denotes a transverse fold line connected to a driving closing means. For example, the illustrated embodiment includes two transverse fold lines 42, 52 both driving.

The closing means 4, 5 are preferably folded toward the outer surface of the base flap 26, i.e. opposite to the covering flap 30, along the transverse fold lines 42, 52 as illustrated in FIG. 7a, in such a way as to leave totally free the covering flap 30 and for example permit a large marking surface on the covering flap 30.

Figure 7B:
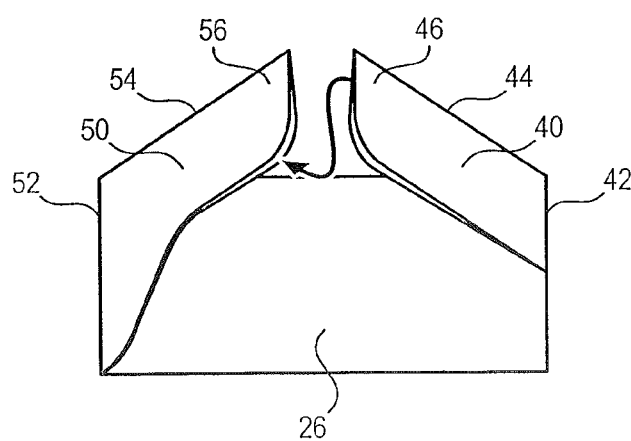

FIG. 7b represents the packaging seen from behind while the closing means 4, 5 are being folded toward the other along their respective transverse fold lines 42, 52. An end section 46, 56 of one of the closing means is then engaged in the dihedron 40, 50 formed by the other closing means.

In the case where the two closing means 4, 5 form a dihedron, each dihedron can be housed in the other dihedron according to choice. In FIG. 7b, it is the right-hand dihedron 44 which is housed in the left-hand dihedron 54. Alternatively the reverse could apply.

Figure 8A:
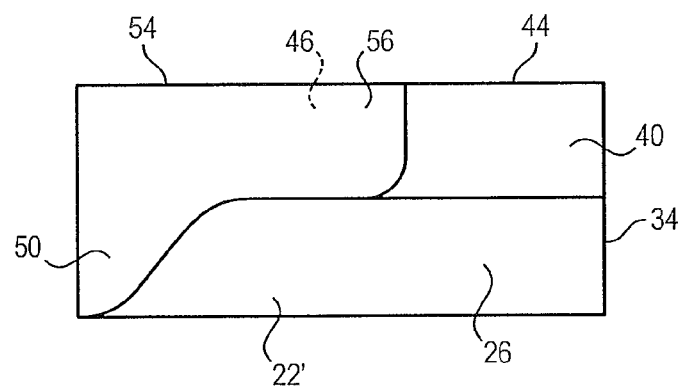
FIGS. 8a and 8b respectively represent a back and front view of the aforementioned packaging in the closed position.
Figure 8B:
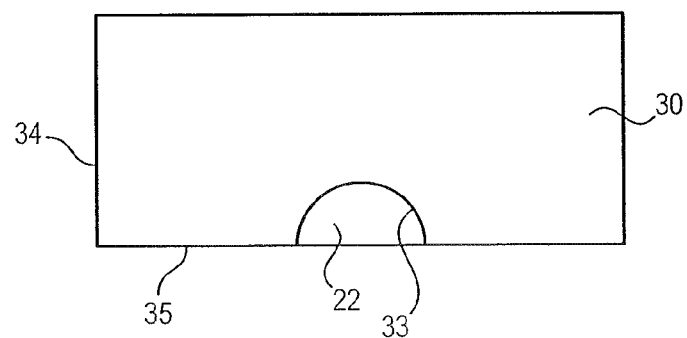

With reference to FIG. 8a, the closing means 4, 5 bear against the outside of the base flap 26, and are only held using this mechanical engagement which holds the packaging 1 closed.

Note that the shape of the closing means 4, 5 is designed to meet both requirements.

Firstly, their respective lengths in the direction of the longitudinal fold line 24 must be adequate to provide the engagement of one in the other.

For example, in the case where the transverse fold lines 42, 52 are perpendicular to the longitudinal fold line 24, the sum of the lengths of the closing means 4, 5 must be greater than the length of the longitudinal fold line 24.

Secondly, the closing means 4, 5 held together must leave uncovered at least a second section of surface 22' of the receiving cradle 2, located on the base flap 26, so that the gripping of the receiving cradle 2 leaves the closing means 4, 5 free. This second uncovered section 22' preferably contains a section symmetrical in relation to the protective fold line 28 to the section 22 of the protective flap 27 left uncovered owing to the notch 33.

Preferably, when both closing means 4, 5 are driving, the transverse fold lines 42, 52 are chosen perpendicular to the longitudinal fold line 24. Thus, when the dihedrons 40, 50 are engaged one inside the other, their respective edges are in contact over at least one segment which improves the rigidity of fastening of the closing means 4, 5.

Provision can be made for placing the contents M in the packaging during the aforementioned folding process, typically before the step of folding the covering flap 30 illustrated in FIG. 6, or for carrying out a phase of fully shaping the packaging by folding as illustrated in FIGS. 2 to 8 then re-opening the packaging in order to introduce the contents M therein before re-closing the packaging.

The opening of the packaging thus prepared will now be detailed with regard to FIGS. 2 and 9a to 9c.

With reference to FIG. 2, a handler takes hold of the packaging manually.

A first hand clamps the receiving cradle 2 on the sections left uncovered, for example his or her index finger on the uncovered section 22' of the base flap 26 left by the dihedrons 40, 50 and his or her thumb on the uncovered section 22 of the protective flap 27 left by the notch 33.

The other hand can then take hold of the free edge 35 of the covering flap 30 and push it away from the receiving cradle 2 to raise the covering flap 30. To make sure of the grip, the handler can slide his or her thumb between the covering flap 30 and the underlying protective flap 27 and thus clamp a gripping area 32 of the covering flap 30 adjacent to the free edge 35.

Note that the section of free transverse edge 34, present on the covering flap 30 permits a peeling of the gripping area 35 without immediately incurring the opening of the packaging 1, since the urging of the covering flap 30 is limited to this free section 34 of the transverse edge, no stress is transmitted to the closing means 4, 5.

Figure 9A:
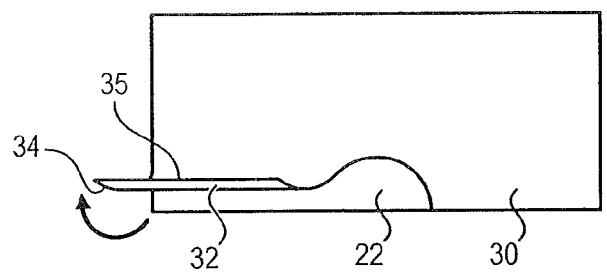
FIGS. 9a to 9c represent different states of a packaging according to the embodiment in FIG. 3 in the process of being opened.
Figure 9B:
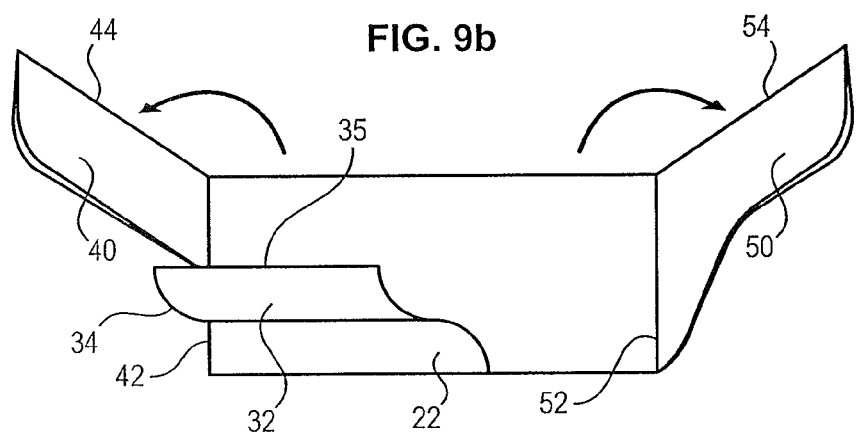

In FIG. 9a, the fingers of the handler are not represented. The free edge 35 of the covering flap 30 is peeled to the left of the notch 33, the free transverse edge section 34 being located on the left-hand side of the covering flap 30.

When the handler raises the covering flap 30, the gripping area 32 stretches and applies a flexion stress on each driving transverse fold line 42, 52. This flexion stress makes each driving closing means 4, 5 undergo a deformation of it dihedron 40, 50 simultaneously in the direction of an opening about the fold lines 44, 54 and of pivoting about the fold lines 42, 52, which incurs its automatic unfolding along the driving transverse fold line 42, 52 associated with it. Beyond a limit angle of rotation of a driving closing means about its driving transverse fold line 42, 52, the other closing means is no longer lodged in its dihedron; the mechanical engagement of the closing means 4, 5 with each other is then broken.

Figure 9C:
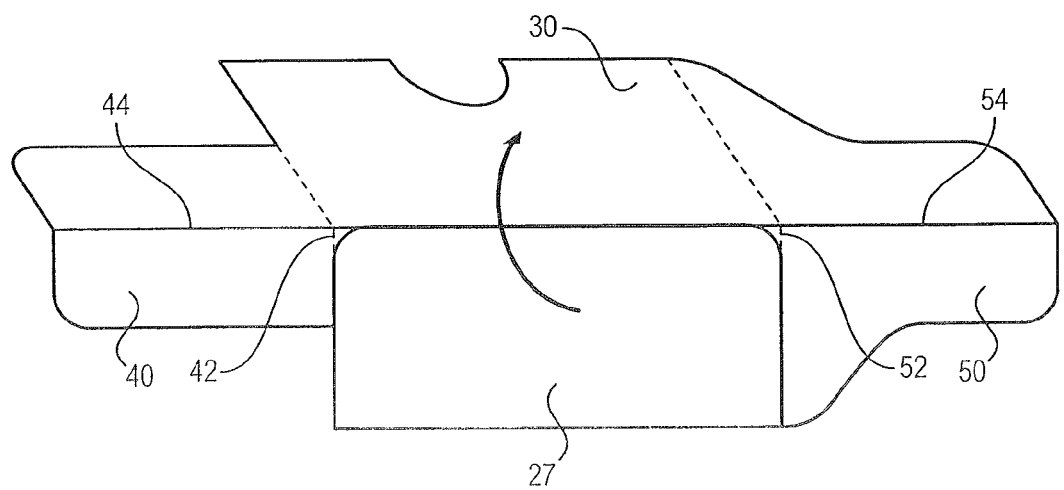

The unfolding of each driving closing means 4, 5 along the driving transverse fold line 42, 52 continues until the extension 44, 54 that traverses it is at least substantially aligned with the longitudinal fold line 24, as illustrated in FIG. 9c.

As previously stated, the raising of the covering flap 30 triggers the unfolding of the cover element 3 along the longitudinal fold line 24, which leads to the unfolding of each dihedron 40, 50 along the fold line 44, 54.

Once the unfolding of the cover element 3 is finished, the handler still has one hand clamping the now uncovered protective cradle 2; he or she can present the packaging 1 to a third-party for the latter to take hold of the contents M encased in the casing 20 using appropriate means, such as sterile tweezers. Alternatively, the handler can perform the extraction of the contents M him or herself with his or her free hand.

To facilitate the extraction of the contents M by a third party, the handler can where applicable apply with his or her free hand a slight flexion to the covering flap 30, to one of the closing means 4, 5 or to the protective flap 27, in such a way as to clear a larger area of access to the casing 20.

Variants

Variant embodiments relating to specific features of the packaging will now be described with reference to FIGS. 10 to 17. These variants can all be combined with one another.

Figure 10:
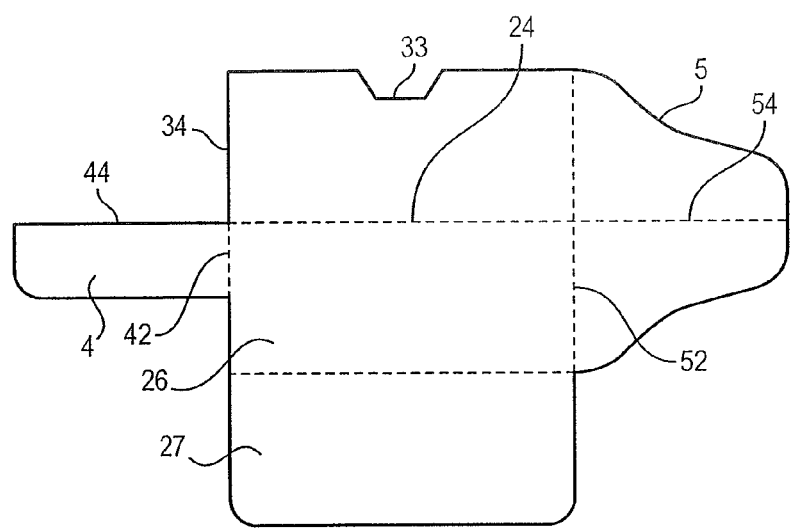
FIGS. 10 to 17 represent variant embodiments of the packaging according to the invention.

In the embodiment illustrated in FIGS. 3 to 8, both closing means 4, 5 are driving. In a variant as illustrated in FIG. 10, the packaging 1 includes a driving closing means 5 and another closing means 4 connected only to the base flap 26. Upon closing the cover element 3, only the driving closing means 5 form a dihedron, whereas the non-driving closing means 4 retains a planar shape subsequently inside the dihedron of the driving closing means 5. The non-driving closing means 4 does not provide any function of transmission of mechanical force during the opening of the packaging: its unfolding along its transverse fold line 42 is mechanically caused by the unfolding of the driving closing means 5 in which it is encased.

Figure 11:
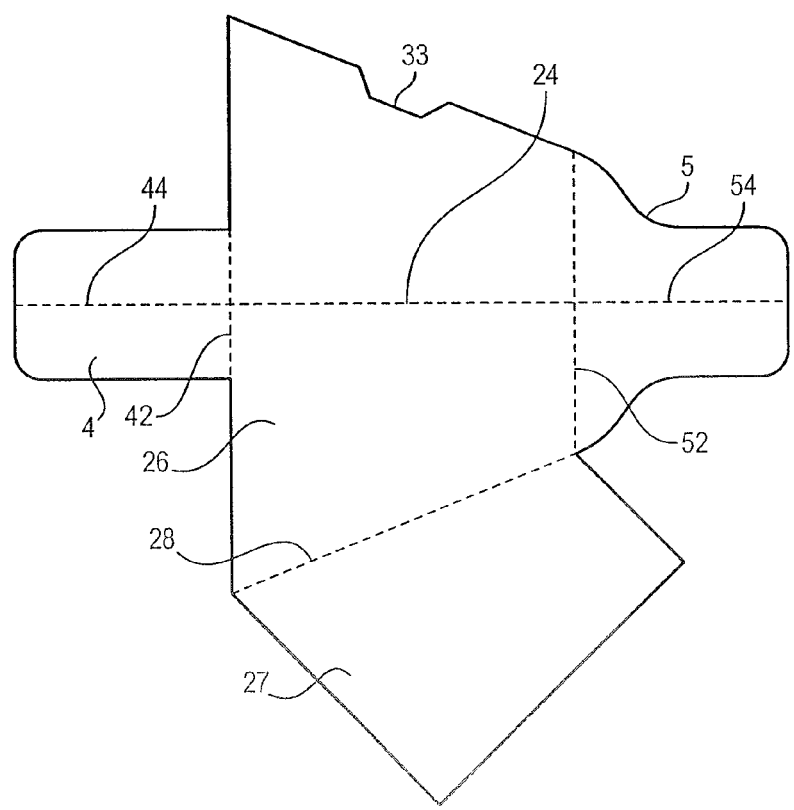

As illustrated in FIG. 11, the packaging in accordance with the present invention is not limited to a rectangular outline. The base flap 26 can for example have the overall shape of a parallelogram, the two protective 27 and covering 30 flaps being hinged on the base flap 26 about the fold lines 24, 28, non-parallel but remaining overall symmetrical to the base flap 26 in relation to these fold lines 24, 28.

Figure 12:
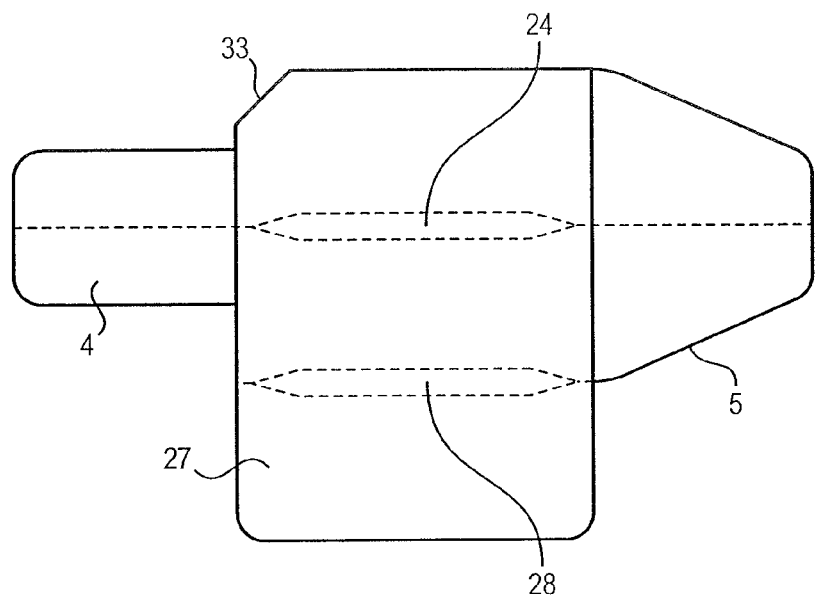

As illustrated in FIG. 12, at least one of the fold lines 24, 28 can be double over at least part of its length to give thickness to the packaging, particularly to the cradle 2 once the packaging has been shaped.

Moreover, the mechanical means of holding without gluing, formed of at least one dihedron according to the previously described embodiment, can be replaced by any equivalent mechanical means, for example the production of at least one longitudinal incision 55 opening onto the free edge of a closing means 5 opposite the hinge line 52 in order to receive the end of the additional closing means 4 as illustrated in FIGS. 14a and 14b.

The closing means 4, 5 can be folded against the base flap 26, as illustrated in FIG. 7a, or in a variant, forward against the covering flap 30 of the cover element 3, as illustrated in FIG. 15. The marking surface on the covering flap 30 is then reduced, but the handler can directly monitor the separation of the closing means 4, 5 and therefore have better visual control of the opening of the packaging 1. Moreover, in this case a marking can be made on the base flap 26.

The notch 33 can be placed substantially in the middle of the free edge 35, as illustrated in FIGS. 2 to 9. In a variant, the notch 33 is placed at the angle of a transverse edge and the free edge 35 of the cover element 3, as illustrated in FIGS. 12 and 16. Thus, the surface sections 22, 22' left uncovered on the receiving cradle 2 are located in a corner of the protective flap 27 and the base flap 26. In another variant illustrated in FIG. 17 the free edge 35 of the covering flap 30 can have a recess 33 which extends continuously between its two ends.

The hole left by the notch 33 as illustrated in FIGS. 2 to 9 is semi-circular. In a variant, this hole can be of polygonal shape (a trapezoid in FIGS. 10 and 11, a triangle in FIG. 12), ovoid, or any other appropriate shape.

Figure 13:
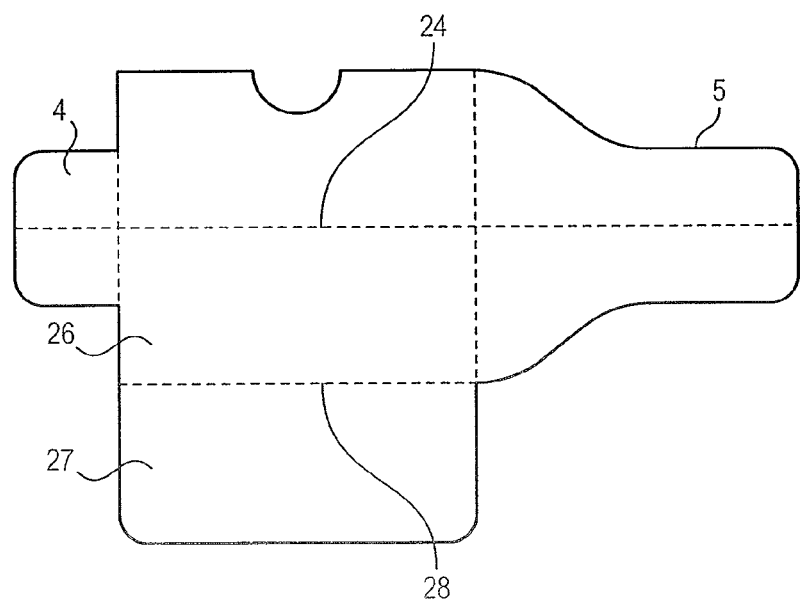

The closing means 4, 5 can have substantially identical lengths in the direction of their fold lines 44, 54, as illustrated in FIG. 3, or else different lengths, as can be seen in the variant embodiment illustrated in FIG. 13.

The protective flap 27 can have a length, taken perpendicular to the protective fold line, 28, substantially equal to that of the base flap 26 as illustrated in FIG. 3, in such a way as to totally cover it by folding along the line 28. In a variant illustrated in FIG. 12, this length of the protective flap 27 can be less than that of the base flap 26, while being greater than the depth of the notch 33 of the covering flap 30 in such a way as to prevent any access to the casing 20 of the cradle 2 when the packaging is in the folded position.

The closing means gradually narrowing into a tapered shape away from the fold line 52 can exhibit curvilinear narrowing, as illustrated in FIG. 3, or straight narrowing, as illustrated in FIG. 12.

Materials Used

The sheet of the packaging is made of a material suitable for housing the contents M, for example contents of gauze tent or knit type. It is therefore possible to use a material of medical grade, compatible with various sterilization methods. This material must protect the contents M mechanically (handling, humidity), provide a microbial barrier in order to maintain the sterility of the contents M and generate as few particles as possible.

To improve the resistance of the sections of the packaging that are subjected to a stress during its opening, the material is preferably tear-resistant, and more flexible than paper. Furthermore, this material is preferably recyclable. Very preferably, this material is a fiber non-woven textile material, for example made of high-density polyethylene. Such a material is known by the name "Tyvek" (registered trademark). One advantage offered by a textile material is that it can exhibit sufficient rigidity to ensure the holding of the closing means 4, 5 engaged one inside the other and is smooth which facilitates opening.

The invention claimed is:

1. A packaging for an item of medical equipment produced by folding a sheet into a folded configuration so as to form: a cradle for receiving a content, wherein the cradle is made of two flaps longitudinally hinged together so as to form a clamp, a cover element hinged on one of the two flaps of the cradle, and first and second means for closing the packaging, wherein the first and second means for closing the packaging are each hinged transversely on at least one of the two flaps of the cradle and the cover element, wherein the first and second means for closing the packaging are designed to be fixed together by simple mechanical engagement between said first and second means for closing the packaging such that, when the packaging is urged to an open configuration, the cover element exerts a force on said first and second means for closing the packaging mechanically engaged with each other, making the first and second means for closing the packaging automatically separate and thus moving the packaging to the open configuration.

2. The packaging according to claim 1, wherein at least one of the first and second means for closing the packaging is hinged transversely on the cover element by a transverse fold line.

3. The packaging according to claim 1, wherein the first means for closing the packaging is hinged transversely on one of the two flaps of the cradle and on the cover element by a first transverse fold line.

4. The packaging according to claim 3, wherein one of the two flaps of the cradle is a base flap, and wherein the cover element is hinged to the base flap of the cradle by a longitudinal fold line wherein the longitudinal fold line intersects the first transverse fold line.

5. The packaging according to claim 4, wherein each of the first and second means for closing the packaging is traversed by an extension of the longitudinal fold line of the cover element on the base flap, allowing each of the first and second means for closing the packaging to form a dihedron when the packaging is in the folded configuration.

6. The packaging according to claim 5, wherein each dihedron is symmetrical with respect to the extension of the longitudinal fold line.

7. The packaging according to claim 4, wherein the second means for closing the packaging is hinged transversely on one of the two flaps of the cradle and on the cover element by a second transverse fold line, wherein each of the first and second means forms a dihedron when the packaging is in the folded configuration, having an edge wherein both the first and second transverse fold lines are perpendicular to the longitudinal fold line of the cover element on the base flap, and wherein said edges touch each other in at least one segment when the first and second means are engaged one inside the other in the folded configuration.

8. The packaging according to claim 1, wherein in the folded configuration of the packaging, mechanical engagement between the first and second means is effected by encasing a section of the second means within a dihedron formed by the first means.

9. The packaging according to claim 1, wherein the cover element includes a covering flap comprising a free edge opposite a longitudinal fold line, wherein in the free edge is formed at least one notch leaving a section of a surface of the cradle uncovered, when the packaging is in the folded configuration.

10. The packaging according to claim 1, wherein the cover element includes a covering flap comprising at least one transverse edge including a transverse section connected to one of the first and second means for closing the packaging and a free transverse section adjacent to a free edge.

11. The packaging according to claim 1, wherein, when the packaging is in the folded configuration, the first and second the means for closing the packaging are folded against and partly cover the cradle in such a way as to leave a section of a first surface on the cradle uncovered.

12. The packaging according to claim 11, wherein the cover element includes a covering flap comprising a free edge opposite a longitudinal fold line, wherein in the free edge is formed at least one notch leaving a section of a second surface of the cradle uncovered, when the packaging is in the folded configuration, and wherein the two flaps of the cradle are a protective flap folded on a base flap by a protective fold line, wherein the section of the first surface and the section of the second surface left uncovered on the cradle extend on either side of the protective fold line so as to be simultaneously taken hold of in a clamping movement.

13. The packaging according to claim 1, wherein said packaging is made of a non-woven textile material.

14. The packing according to claim 1, wherein said packaging is made of polyethylene fibers.

\* \* \* \* \*